US005591573A

United States Patent [19]

Whalen et al.

[11] Patent Number: 5,591,573

[45] Date of Patent: Jan. 7, 1997

[54] METHOD AND SYSTEM FOR TESTING BLOOD SAMPLES

[75] Inventors: John J. Whalen; Michael E. Chlebowski, both of Pasadena; Charles M. Heldebrant, Arcadia; H. Edward Matveld, North Hollywood, all of Calif.

[73] Assignee: Alpha Therapeutic Corporation, Los Angeles, Calif.

[21] Appl. No.: 419,620

[22] Filed: Apr. 10, 1995

[51] Int. Cl.[6] .............................. C12Q 1/70; C12P 19/34; C12N 7/00

[52] U.S. Cl. .......................... 435/5; 435/91.2; 435/235.1; 604/409; 604/410

[58] Field of Search ..................................... 604/409, 410; 422/68.1; 73/864.81; 210/206

[56] References Cited

U.S. PATENT DOCUMENTS

| | | | |
|---|---|---|---|
| 4,527,383 | 7/1985 | Bingham | 57/200 |
| 4,820,297 | 4/1989 | Kaufman et al. | 604/409 |
| 4,846,005 | 7/1989 | Bacehowski et al. | 73/864.81 |
| 4,900,321 | 2/1990 | Kaufman et al. | 604/409 |
| 5,176,995 | 6/1993 | Snisky et al. | 435/6 |
| 5,364,526 | 11/1994 | Matkovich et al. | 210/206 |
| 5,423,792 | 6/1995 | Oxley | 604/409 |

FOREIGN PATENT DOCUMENTS

| | | | |
|---|---|---|---|
| 0248690A1 | 5/1987 | France | C12Q 1/70 |
| WO93/16201 | 8/1993 | WIPO | C12Q 1/70 |

OTHER PUBLICATIONS

Matsuda J. et al., Preliminary Report on an Automated Screening Test for Detection of Antibody to Human Immunodeficiency Virus Type 1 in Whole Blood. *Clinical Infectious Diseases* 19:327–8 1994.

Kim, H–S., Smithies, O., Recombinant Fragment Assay for Gene Targeting Based on the Polymerase Chain Reaction. *Nucleic Acids Research* 16:8887–8903 1988.

Gresser, I., ed., *Interferon 1981 vol. 3,* Academic Press, NY, 1981, p. 102.

*Primary Examiner*—W. Gary Jones

*Assistant Examiner*—Amy Atzel

*Attorney, Agent, or Firm*—Christie, Parker & Hale, LLP

[57] ABSTRACT

Systems, processes and devices are provided which are useful for testing blood or plasma donations to detect those specific donations which are contaminated by virus above a predetermined level. An apparatus and process is described which forms individual, separately sealed, and connected sample-containing pouches from a flexible hollow tubing segment connected to a fluid donation container. The tubing segment is sealed at spaced-apart intervals along its length, with tubing segment portions in the intervals between the seals defining pouches, each of which contains a portion of a plasma sample. The contents of the pouches are formed into pools which are subsequently tested for virus contamination by a high sensitivity test such as PCR. When a pool tests positive, indicating it is contaminated by a virus, a further pouch is removed from each of the tubing segments used to form the initial pool. Subsequent pouches are divided into approximately equal sized subgroups and their contents separately formed into subpools. A selected one of the subgroup pools is then tested for virus contamination. The test process is iterated, with each pool that tests positive being further subdivided into two successively smaller subgroups, until two final subgroups are formed, each comprising a single pouch corresponding to a single plasma donation. The final two pouches are subsequently PCR tested in order to determine and uniquely identify the corresponding contaminated donation.

31 Claims, 8 Drawing Sheets

METHOD AND SYSTEM FOR TESTING BLOOD SAMPLES

FIELD OF THE INVENTION

The present invention relates generally to systems and processes for preparing and analyzing samples taken from plasma donations to uniquely identify donations which are virus contaminated. In particular, the invention relates to an apparatus and process for forming individual, separately sealed, and connected sample-containing pouches from a tubing segment containing the same plasma as is contained in the donation. The invention also relates to a process of forming initial screening test pools from the pouches, testing the pools for the presence of a virus, and then testing only selected subpools to identify individual contaminated donations.

BACKGROUND OF THE INVENTION

Blood, plasma, and biological fluid donation programs are essential first steps in the manufacture of pharmaceutical and blood products that improve the quality of life and that are used to save lives in a variety of traumatic situations. Such products are used for the treatment of immunologic disorders, for the treatment of hemophilia, and are also used in maintaining and restoring blood volume in surgical procedures and other treatment protocols. The therapeutic uses of blood, plasma, and biological fluids require that donations of these materials be as free as possible from viral contamination. Typically, a serology test sample from each individual blood, plasma, or other fluid donation is tested for various antibodies, which are elicited in response to specific viruses, such as hepatitis-C (HCV) and two forms of the human immunodeficiency virus (HIV-1 and HIV-2). In addition, the serology test sample may be tested for antigens designated for specific viruses such as hepatitis-B (HBV), as well as antibodies elicited in response to such viruses. If the sample is serology positive for the presence of either specific antibodies or antigens, the donation is excluded from further use.

Whereas an antigen test for certain viruses, such as hepatitis-B, is thought to be closely correlated with infectivity, antibody tests are not. It has long been known that a blood plasma donor may, in fact, be infected with a virus while testing serology negative for antibodies related to that virus. For example, a window exists between the time that a donor may become infected with a virus and the appearance of antibodies, elicited in response to that virus, in the donor's system. The time period between the first occurrence of a virus in the blood and the presence of detectable antibodies elicited in response to that virus is known as the "window period." In the case of HIV, the average window period is approximately 22 days, while for HCV, the average window period has been estimated at approximately 98 days. Therefore, tests directed to the detection of antibodies, may give a false indication for an infected donor if performed during the window period, i.e., the period between viral infection and the production of antibodies. Moreover, even though conventional testing for HBV includes tests for both antibodies and antigens, testing by more sensitive methods have confirmed the presence of the HBV virus in samples which were negative in the HBV antigen test.

One method of testing donations, which have passed available antibody and antigen tests, in order to further ensure their freedom from incipient viral contamination, involves testing the donations by a polymerase chain reaction (PCR) method. PCR is a highly sensitive method for detecting the presence of specific DNA or RNA sequences related to a virus of interest in a biological material by amplifying the viral genome. Because the PCR test is directed to detecting the presence of an essential component of the virus itself, its presence in a donor may be found almost immediately after infection. There is, theoretically therefore, no window period during which a test may give a false indication of freedom of infectivity. A suitable description of the methodology and practical application of PCR testing is contained in U.S. Pat. No. 5,176,995, the disclosure of which is expressly incorporated herein by reference.

PCR testing is, however, very expensive and since the general donor population includes a relatively small number of PCR positive donors, individual testing of each donation is not cost effective or economically feasible. Hence, an efficient and cost effective method of testing large numbers of blood or plasma donations to eliminate units having a viral contamination above a pre-determined level is required.

One method of testing a large number of plasma donations is to pool a number of individual plasma donations. The pool is then PCR tested and the individual donations comprising the pool are either retained or disposed of, depending on the outcome of the PCR test. While reducing the number of PCR tests, and the costs associated therewith, this method results in a substantial waste of a significant portion of virus free donations. Since only a single donation with a viral contamination above a pre-determined level will cause a pool to test PCR positive, the remaining donations that contribute to a pool may well be individually PCR negative. This result is highly probable given that a relatively small number of PCR positive donors exist in the general donor population. In the conventional pooling approach, all donations comprising the pool are disposed of upon a PCR positive result, including those donations that are individually PCR negative.

In addition, plasma donations are often frozen soon after they are received. When samples of individual plasma donations are needed for pooling, each donation must be thawed, an aliquot of the blood or plasma removed from the donation, and the donation must then be refrozen for preservation. Multiple freeze-thaw cycles may adversely affect the recovery of the RNA or DNA of interest as well as the proteins contained within the plasma, thus adversely affecting the integrity of the PCR test. Moreover, each time an aliquot of individual plasma donations is withdrawn to form a pool, the donation is subject to contamination, both from the surrounding environment, and from the apparatus used to withdraw the aliquot. Further, if the donation contains a virus, it can contaminate other donations. In order to avoid introducing viral contaminants into an otherwise viral free donation, the sample taking apparatus must be either sterilized after each individual use, or used for taking only a single aliquot from a single individual donation and a new sample taking apparatus used for taking an aliquot from a subsequent individual donation. Either of these methods involves considerable expense and is quite time consuming.

Accordingly, there is a need for a process and system for obtaining multiple blood or plasma samples from individual donations such that particular samples may be pooled without contaminating the remaining samples. It is also desirable that the process and system provide for efficient and cost-effective testing of the blood or plasma donations to identify only uniquely PCR positive donations.

SUMMARY OF THE INVENTION

There is, therefore, provided in the practice of this invention a cost effective and efficient process for preparing and testing samples from a multiplicity of blood or plasma donations to uniquely identify donations which are infected with virus as well as systems and devices for practicing the process.

The process of the present invention results in blood and plasma products being substantially safer because one can readily test for virus contamination in the blood or plasma supply directly. Cost effective, high sensitivity testing can be performed immediately, and contaminated donations identified, without regard to an infectivity window period.

In one embodiment of practice of the present invention, the process comprises the steps of providing a blood or plasma donation in a collection container. A flexible hollow tube is connected to the container and is open to the inside of the container. The tubing segment is filled with blood or plasma from the collection container, and a portion of the tubing segment is sealed at both ends. The sealed portion of the tubing segment is removed from the container and, either before or after the sealed tubing segment portion is removed, a plurality of spaced-apart seals are provided at intervals along the length of the tubing segment between the sealed ends. The segment portions in the intervals between adjacent seals define pouches, wherein each such pouch contains a plasma or blood sample, and wherein the intervals between seals provide a sufficient volume in each such pouch for the planned testing.

In a more detailed embodiment of the present invention, individual plasma donations are collected in a plasma collection bottle which has a testing container connected thereto by a flexible hollow tubing segment. After being filled with a donor's plasma the plasma bottle is tipped so as to transfer plasma to the testing container and the flexible tubing segment, thereby filling the tubing segment. The tubing segment is sealed at spaced-apart intervals along its length, the tubing segment portions in the intervals between the seals define pouches each of which contains a sample of the plasma donation. The tubing segment, which has been converted into a series of pouches, is then disconnected from the plasma collection bottle and frozen until needed for testing.

In a further aspect of the present invention a device for providing multiple heat seals along the length of the tubing segment filled with the blood or plasma donation comprises first and second opposed seal platens. Each seal platen includes a plurality of spaced-apart raised portions along its length alternating with recessed portions. The raised and recessed portions on the first platen are in registry with corresponding raised and recessed portions on the second platen. The opposed seal platens are moved together onto a plastic tubing segment filled with the blood or plasma donation to form heat seals on those portions of the tubing segment compressed between the raised portions and to form chambers defined by opposed recessed portions. The heat seals define a plurality of individual and sequential pouches therebetween and each chamber, defined by each closed pair of recessed portions, is configured to house a pouch.

In yet a further embodiment of the invention, a system for collecting and preparing plasma samples for testing comprises a plasma collection container and a hollow plastic tube connected to the container, each of which are constructed of plastic and each of which contain coded indicia molded into the plastic. The coded indicia are disposed along the major axis of the tubing segment and the code repeats at spaced-apart intervals so that the tubing segment can be provided with a plurality of spaced apart seals along its length to thereby define pouches between the seals. The code intervals of the indicia correspond to the intervals of the pouches, so that each pouch will contain at least one cycle of the code.

To begin the testing process of the present invention, a first pouch is removed from each of a group of tubing segments corresponding to a plurality of separate plasma donations. A portion of the contents of each such first pouch is withdrawn and the contents formed into a pool in a container.

In an exemplary embodiment of the present invention, the first pool is tested for a viral indication. When the first pool tests positive for a viral indication, a next, or second, sequential pouch is removed from each of the tubing segments that were used to form the first pool. The second pouches are divided into two approximately equal subgroups, and the contents of one of the subgroup pools is tested for the presence of a specific virus. When the tested subgroup pool tests negative for the virus, a further sequential pouch is removed from corresponding tubing segments used to form the untested subgroup. The pouches are divided into two approximately equal next generation subgroups, and the contents of the subgroup pouches are formed into pools. One of the next generation subgroup pools is tested for a viral indication.

When the tested subgroup pool tests positive for such viral indication, a pouch is removed from corresponding tubing segments used to form the tested subgroup. The process is iterated, with each positive pool being further subdivided into successively smaller subgroups, with each of the successive subgroups comprising a fraction of the samples of the preceding positive subgroup, until the final pouch corresponding to a single plasma donation is identified.

BRIEF DESCRIPTION OF THE DRAWINGS

These and other features, aspects, and advantages of the present invention will be more fully understood when considered with respect to the following detailed description, appended claims, and accompanying drawings, wherein:

Figure 2:
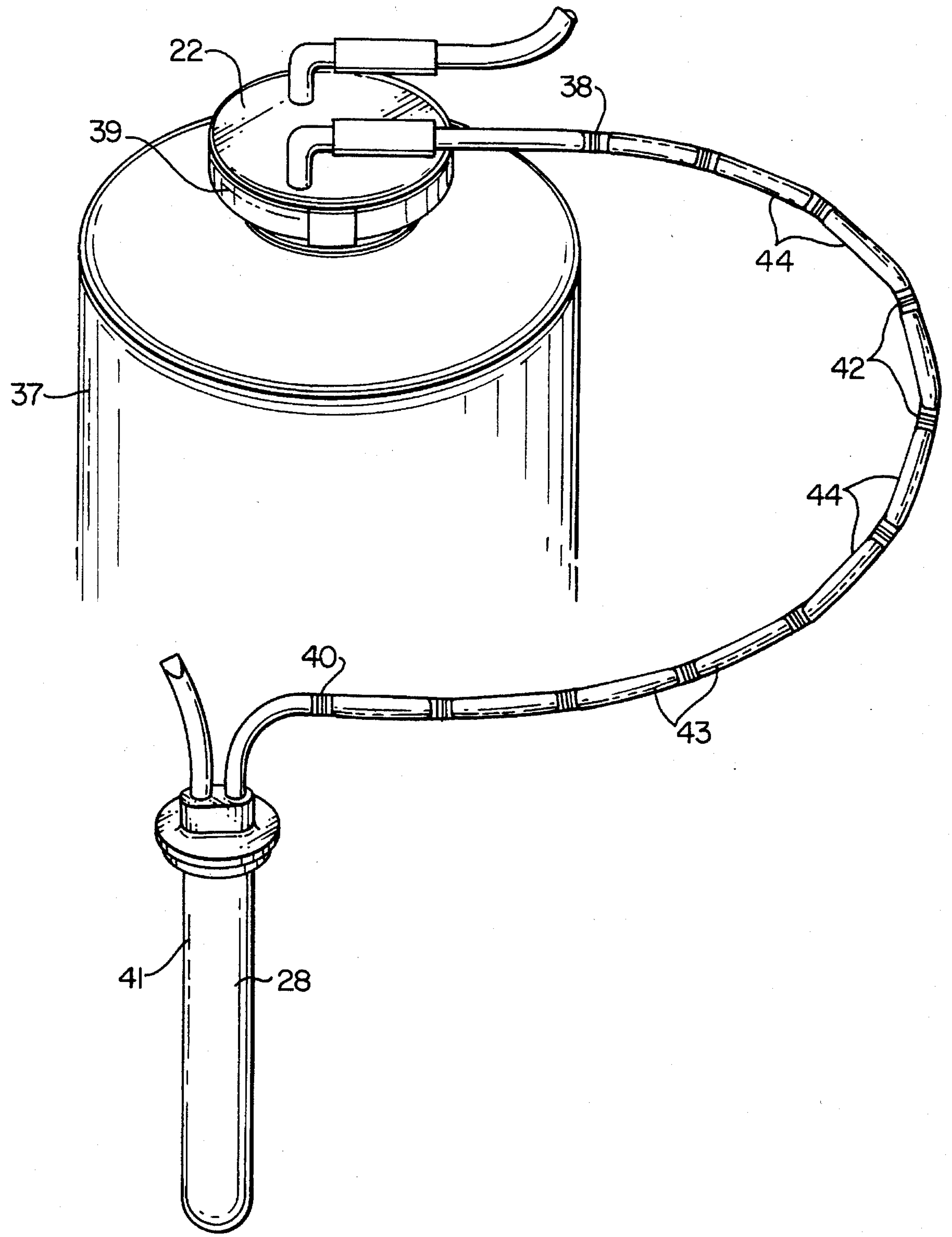
FIG. 2 is a semi-schematic perspective view of a tubing segment connected between a plasma donation bottle and sample container and divided into pouches in accordance with the present invention.

FIG. **3*a* is an enlarged top plan view of a portion of the tubing segment shown in FIG. 2** showing additional details of the seals which separate the pouches.

FIG. **3*b*** is a semi-schematic cross-sectional view of a tubing segment seal.

Figure 4:
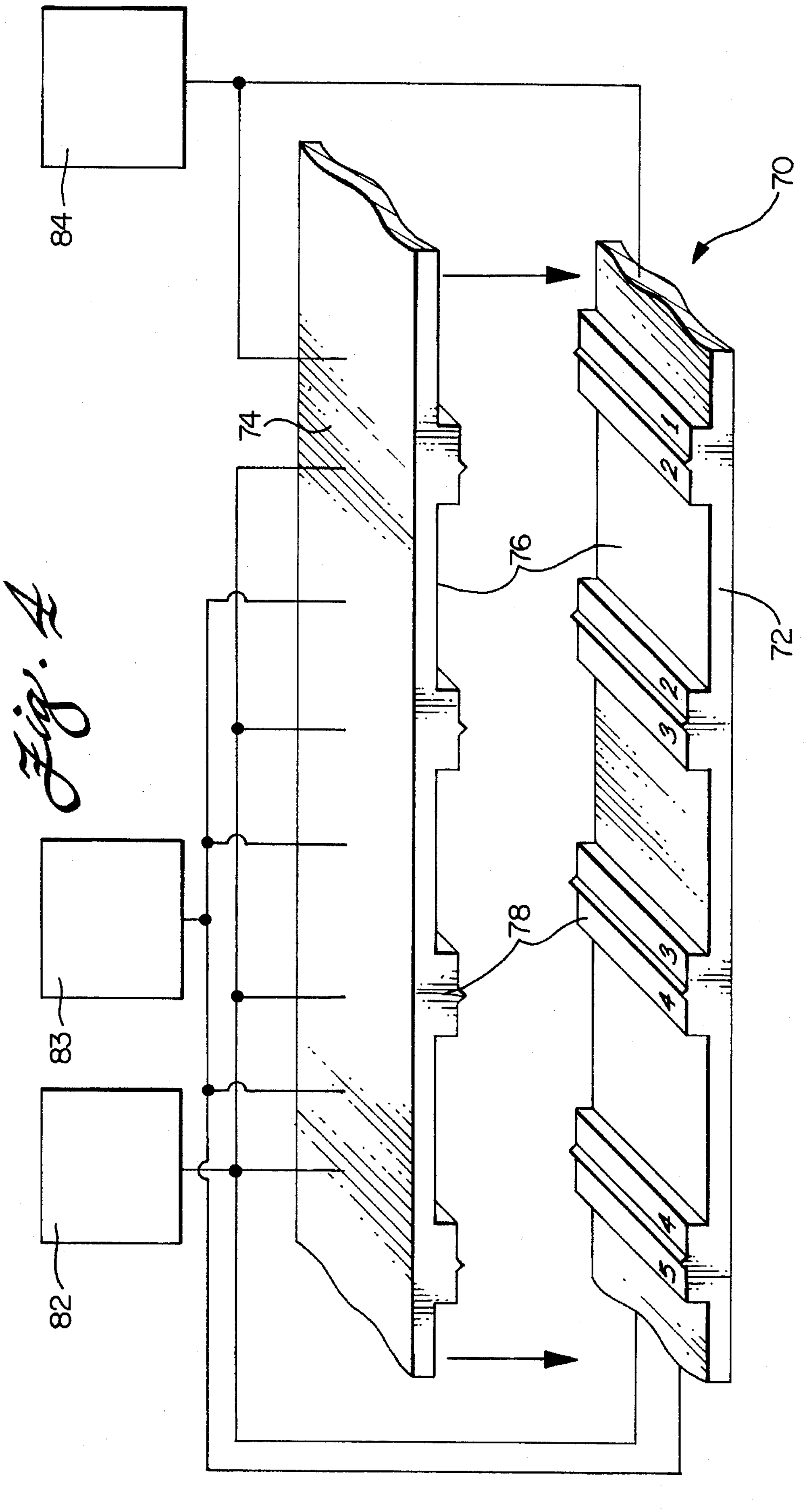

FIG. 4 is a semi-schematic perspective view of a device provided in accordance with practice of the present invention for sealing a tubing into individual pouches.

Figure 5:
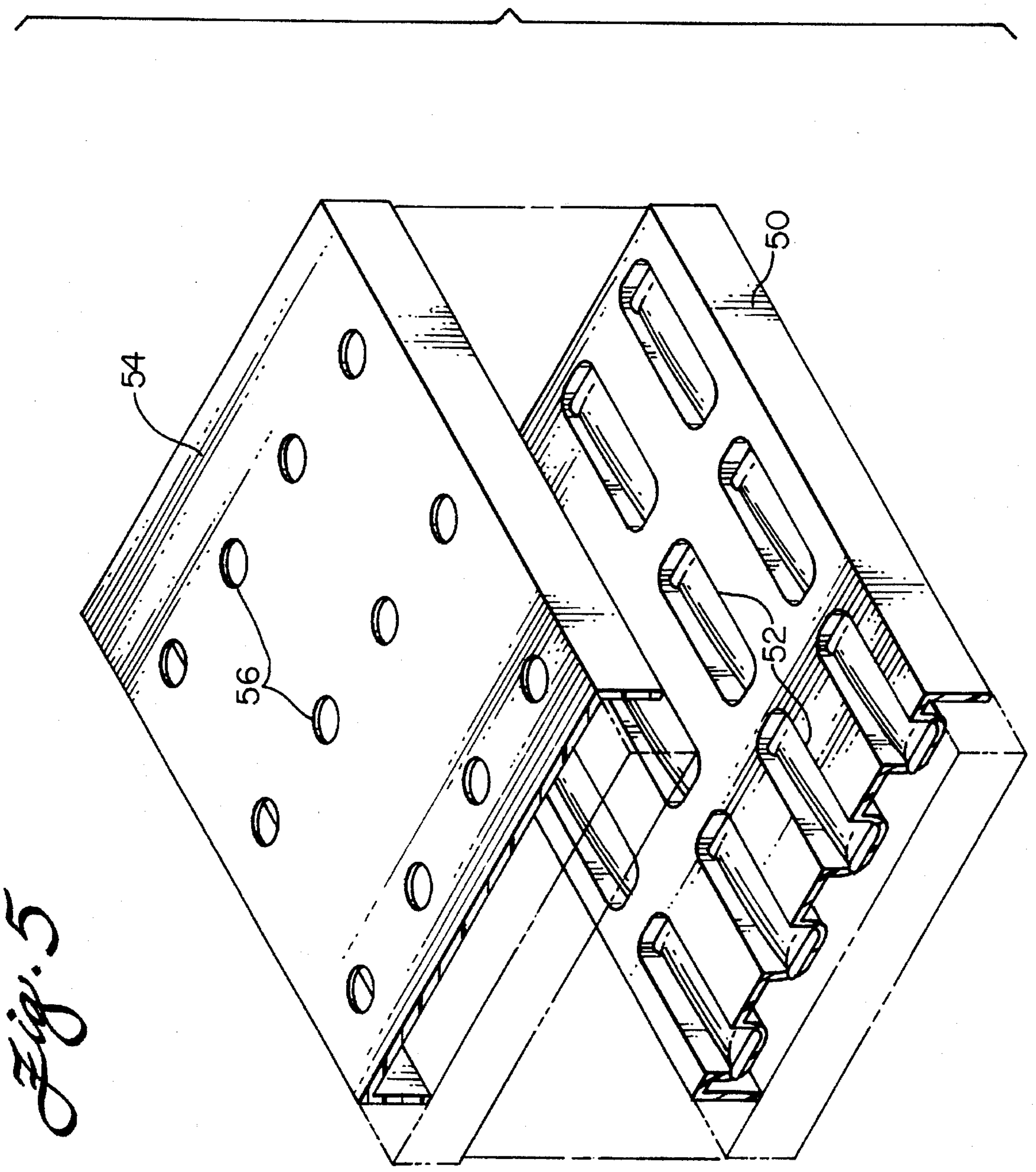

FIG. 5 is a semi-schematic perspective view of a sampling plate and cover provided in accordance with the present invention.

Figure 6:
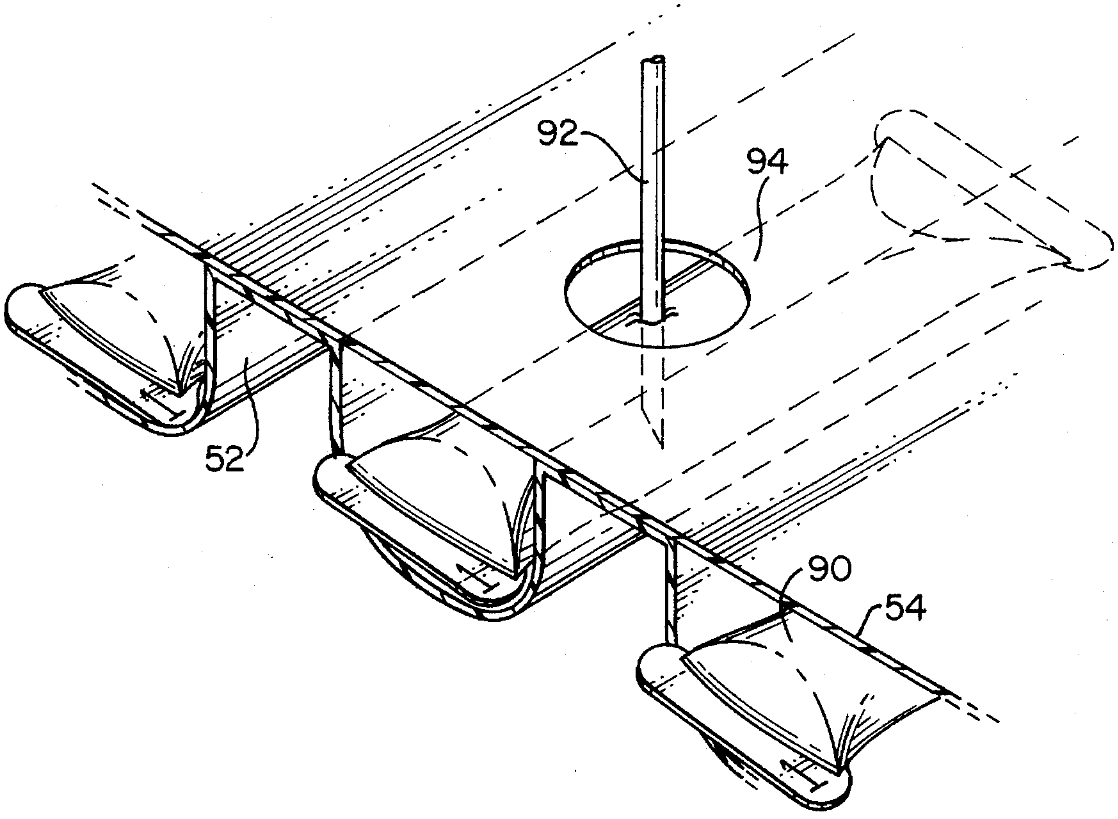

FIG. 6 is a semi-schematic partial cross-sectional view of a plasma pouch contained in a sampling plate sample well provided in accordance with the present invention.

Figure 7:
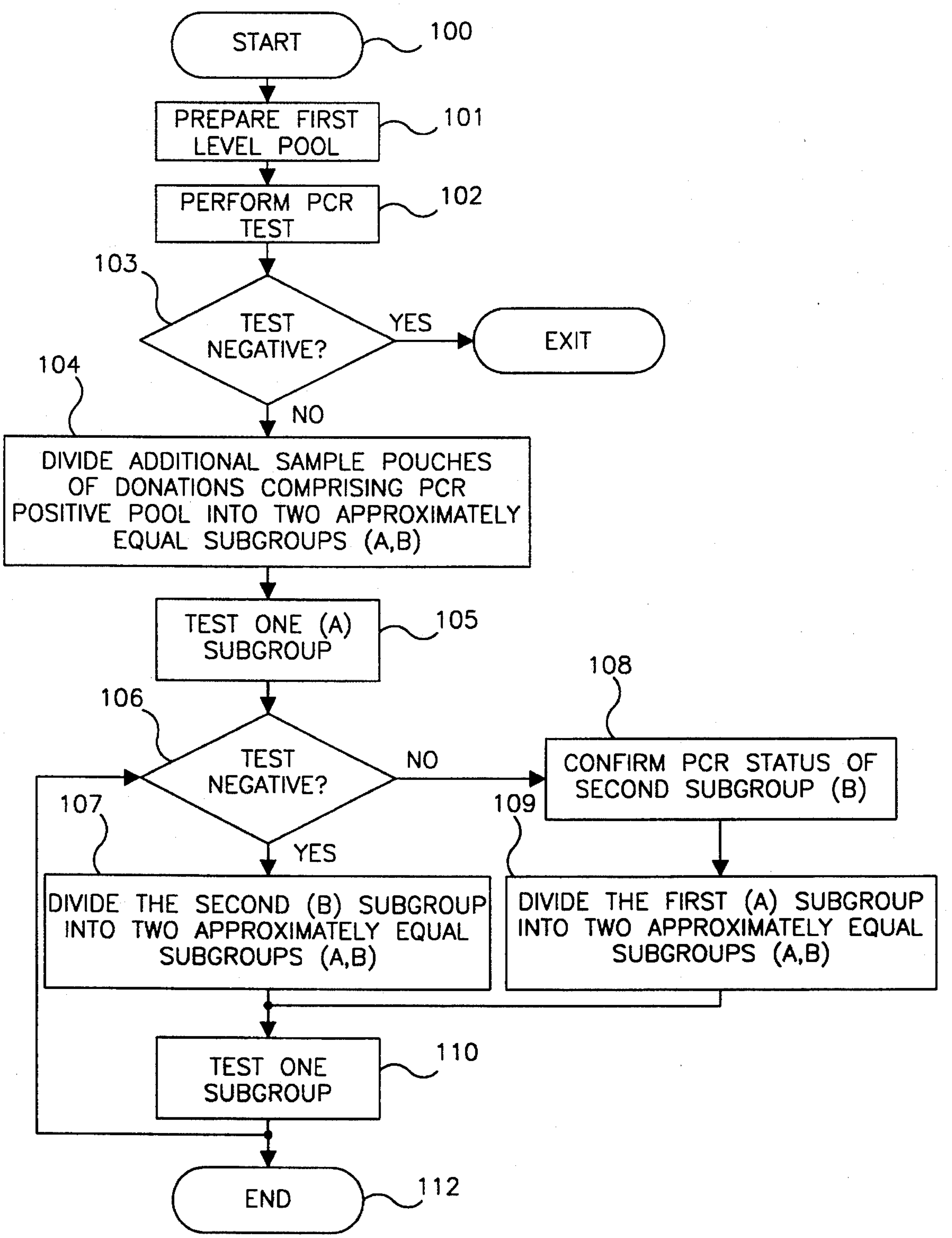

FIG. 7 is a flow chart depicting the test methodology according to the invention for determining PCR positive donors from a donation pool.

Figure 8:
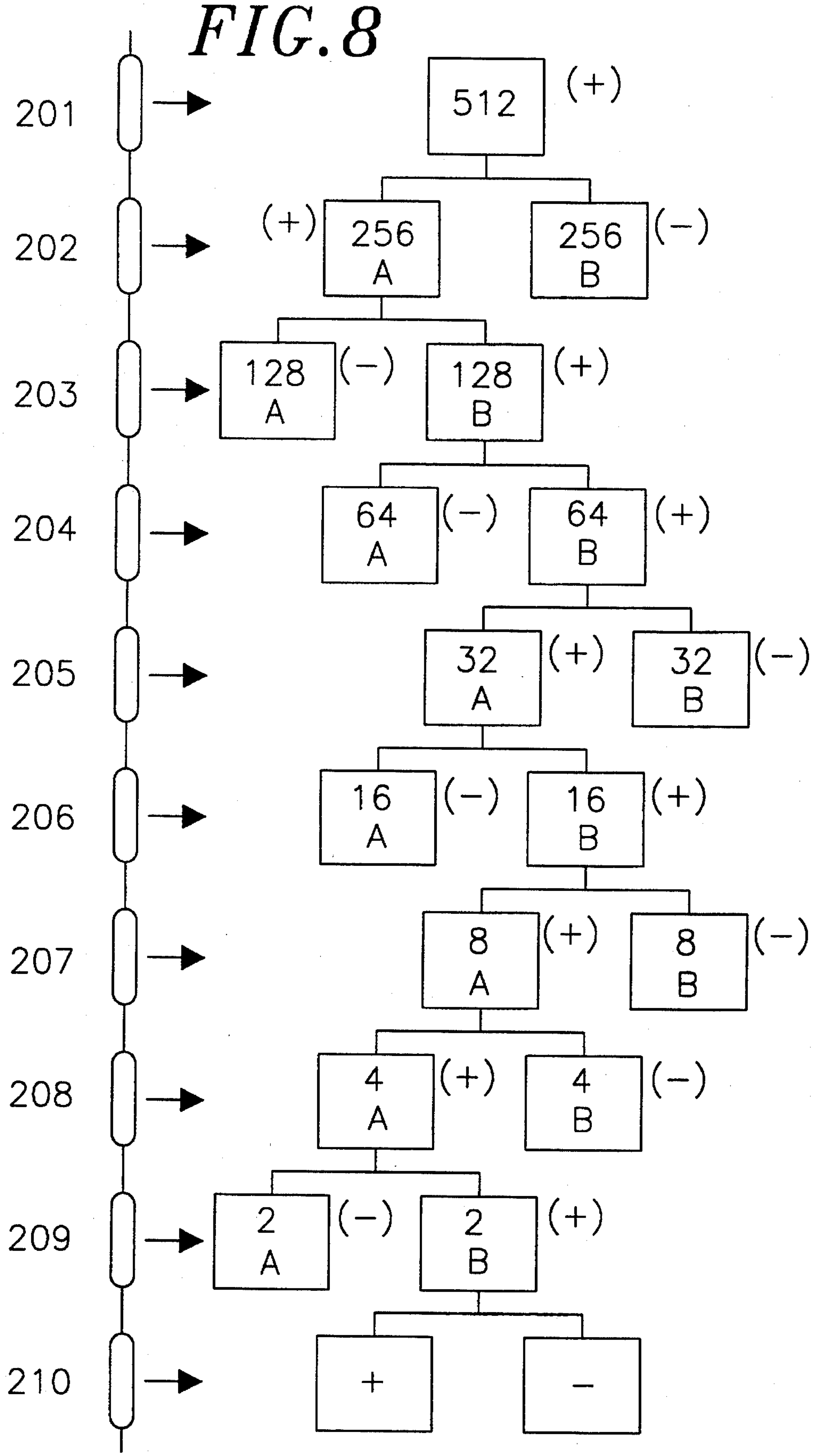

FIG. 8 is a flow chart depicting a test sequence according to the invention for identifying a single PCR positive donation from a 512 donation pool.

DETAILED DESCRIPTION

The present invention relates to systems, processes and devices useful for testing blood or plasma donations to detect those specific donations which have a viral contamination above a pre-determined level. Such contaminated donations are then disposed of to thereby prevent their incorporation into the raw material stream for pharmaceutical products or their transfusion into human patients. The viral detection tests used in accordance with practice of the present invention can be any that directly detect a virus instead of antibodies elicited in response to the virus. The tests include polymerase chain reaction (PCR) tests and other tests which are sufficiently sensitive to directly detect a virus even after pooling samples from multiple donations.

In one embodiment of practice of the present invention, a plurality of separate blood or plasma donations are provided. A blood or plasma sample is drawn from each donation into a corresponding flexible, hollow tubing segment. A plurality of spaced-apart seals are provided at intervals along the length of the tubing segment, so that segment portions in the intervals between seals define pouches where each pouch contains a blood or plasma sample. As is discussed below in greater detail, a unique methodology is provided in accordance with the present invention for testing plasma samples from the pouches after the samples are formed into pools to thereby efficiently and effectively detect and isolate any such blood or plasma donation which is contaminated with virus.

Figure 1:
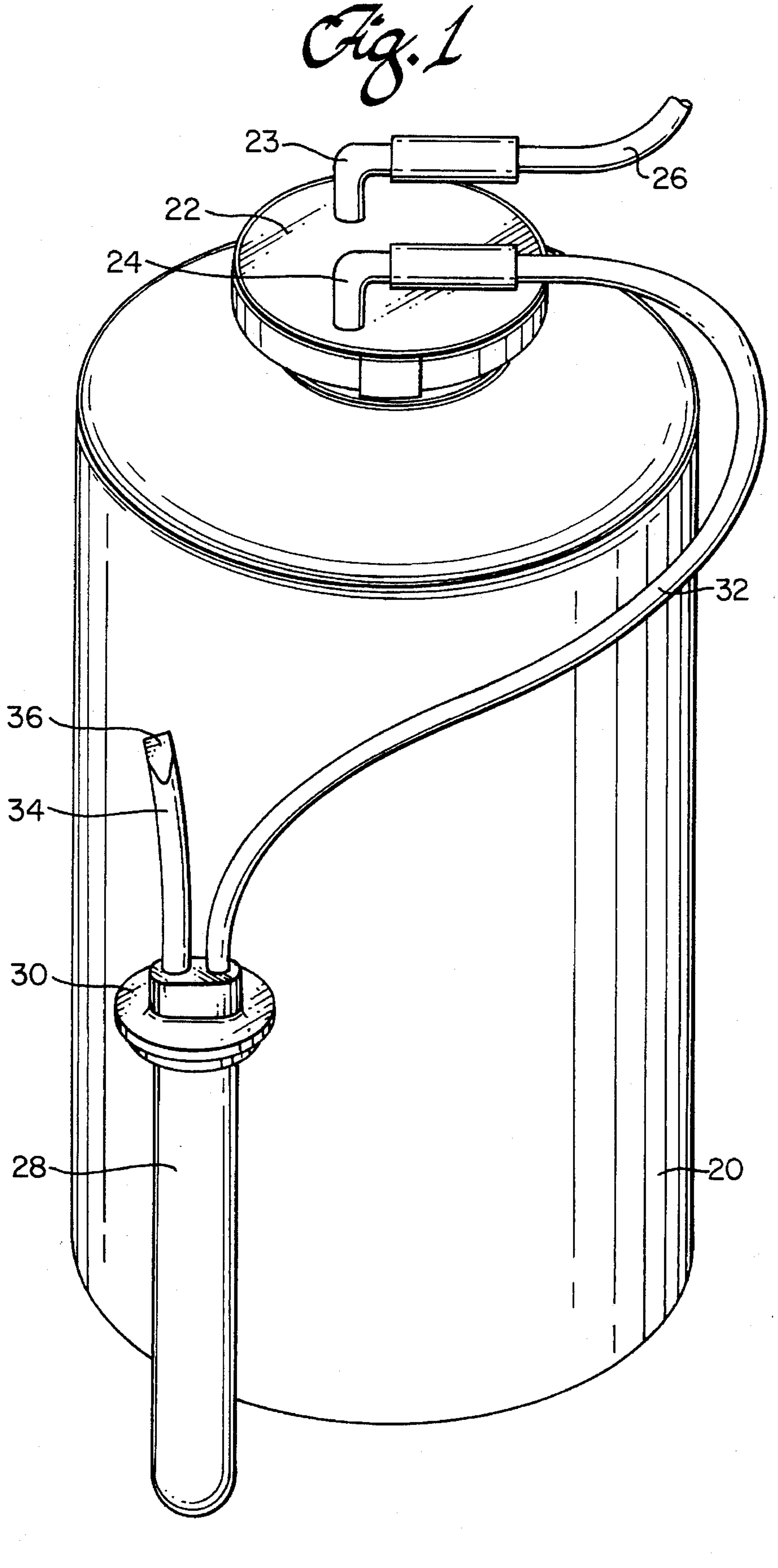
FIG. 1 is a semi-schematic perspective view of one example of a plasma donation bottle and sample container attached by a tubing segment useful in the practice of the present invention.

Turning to FIG. 1, an exemplary embodiment of a system provided in accordance with practice of the present invention for effecting the sampling process is shown. The system includes a standard plasma donation container 20, constructed of a nonreactive material such as polyvinyl chloride (PVC). The donation container 20 includes a cap 22 having two hollow elbow shaped fittings, 23 and 24 respectively, attached to the top surface thereof. The fittings communicate with the interior of the donation bottle through orifices provided in cap 22 for such purpose. A flexible hollow filler tube 26, constructed of a biologically neutral material, such as PVC plastic, is connected at one end to the elbow fitting 23 and connected at the other end to, for example, a needle which is inserted into a donor in order to procure a donation. In the illustrated embodiment, a test container 28, is also provided, for collecting a sample from the donation to be serology tested. The test container 28 is generally test tube shaped and is also constructed of a biologically nonreactive material. The test container 28 includes an integral cap member 30 through which orifices are provided in order to communicate with the interior of the test container.

A flexible hollow tubing segment 32, constructed of a biologically nonreactive plastic material, is connected between the cap member 30 of the test container 28 and the hollow elbow fitting 24 of the plasma donation container cap. The tubing segment 32 is connected to the cap member 30 in a manner such that fluid passing through the tubing segment will enter the test container 28 through an orifice provided in the cap member 30 for such purpose. The tubing segment 32 may be friction fit into said orifice, sonically welded thereto, or otherwise attached in a coaxial relationship with the orifice by techniques well understood by those skilled in the art.

A second orifice may also be provided in the cap member 30, to which a vent tube 34 is connected in a manner similar to tubing segment 32. The vent tube 34 is typically no more than one to two inches in length, and is typically terminated with an inserted, friction fit bacteria excluding filter 36.

In an exemplary embodiment, a blood or plasma donation is withdrawn from a donor and collected in the plasma donation container 20 for subsequent storage until needed. In the case of a plasma donation, blood is typically withdrawn from a donor and passed through a continuous centrifuge apparatus, wherein red blood cells are centrifuged out from the supporting plasma fluid and returned to the donor. The plasma is then collected.

After a plasma donation is taken from a donor and the donation container 20 is filled, the donation container is tilted so as to raise the fluid level over the elbow fitting 24 connected to the tubing segment 32. Plasma enters the tubing segment, flows through the tubing segment, and fills the test container 28. During filling, air trapped within test container 28 escapes through the vent tube 34, allowing the test container to be filled completely. The bacteria excluding filter 36 filters out any bacteria in the returning air, thus preventing contamination of the sample by the surrounding environment. After the test container is filled, plasma from the donation is allowed to fill the tubing segment 32.

Turning now to FIG. 2, after the plasma sample from the donation is drawn into the tubing segment 32, the tubing segment is sealed by a heat weld 38 or other suitable sealing means such as a sonic weld, at a location proximate to the tubing segment's connection to the plasma donation container. A further heat seal 40 is applied to the tubing segment at a location proximate to the segment's connection to the test container 28. An elongated hollow tube, closed off at both ends, and containing a quantity of the plasma donation is thus provided.

The filled portion of the tubing segment 32 is removed from the plasma donation and test containers by cutting the tubing segment away through the center of the seals, 38 and 40. The separate plasma donation container is then removed for freezing and storage, while the separated test container is removed to a laboratory for serology testing. Typically, the contents are tested for various antibodies, which are elicited in response to specific viruses, such as hepatitis-C (HCV), or HIV-1 and HIV-2.

Additional seals 42 are also provided at spaced-apart intervals along the length of the tubing segment, to define sequential individual and connected pouches, each suitably comprising a hollow tubing segment portion 44. Each such portion 44 contains a particular quantity of blood or plasma needed for the specific generation pool to be formed. For example, for pouches to be formed for PCR testing, approximately 0.02 to 0.5 ml of blood or plasma from the host donation may be sealed.

The tubing segment is sealed in a manner to provide from 5 to 15, individual and connected pouches. Sealing, to define the pouches, may be done, either after the tubing segment has been removed from between the plasma donation container and the serology test container, or may be done while the tubing segment is still attached. Sealing may be done by any known method, such as thermo compression sealing (heat sealing), sonic welding or the like, so long as the length of the region compressed and sealed is sufficient to permit the connected pouches to be separated from one another by cutting through the center of the seal, without violating the integrity of the pouch on either side, as indicated more clearly in FIGS. **3*a* and 3*b***.

Turning now to FIGS. **3*a* and 3*b*, in a preferred embodiment the seal between pouches includes a flat pad area 46, including a central narrow portion 47 through which the seal is cut or torn in order to separate the connected pouches. Cutting is done through the central portion in order to insure that each separated pouch remains sealed at compressed tab portions 48** at either end after separation. The length of the seal pad may be made greater or smaller, depending on the chosen separation method. Separation may be done by use of a scalpel, a guillotine cutter, or a simple pair of scissors.

Turning to FIG. 4, an exemplary embodiment of a sealing device 70, useful for providing pouches of specific desired sizes, including means to easily separate the pouches and identify their sequence number along a segment, is shown. The sealing device 70 suitably comprises opposed first and second platens, 72 and 74 respectively, each including a plurality of raised, seal head portions 78, arranged in a spaced apart relationship on the opposing surfaces of the platen. The sealing device 70 is preferably constructed such that the raised portions 78 are movable along their respective platen such that the spacing from one raised seal head portion to another may be varied. The raised seal heads may be arranged along the platen such that the distance between successive seal heads is made progressively smaller so that sealing is performed along the length of a tubing segment at progressively closer spaced intervals. Thus, sample pouches of progressively smaller size and, therefore, progressively smaller volume content may be formed by moving pairs of opposed seal heads along their respective platens to a desired location.

In order to form multiple heat seals along the length of the plastic tubing segment filled with a blood or plasma sample, the tubing segment is placed within the sealing device 70 between the upper and lower sealing platens, 74 and 72 respectively. The opposed platens are brought into proximity with one another thus, compressing and sealing the tubing segments. As depicted in FIG. 4, the plurality of spaced-apart extended, or raised, seal head portions 78, along the length of each platen, alternate with recessed portions 76. As the opposed platens are moved together to form heat seals on those portions of a plastic tubing segment filled with a blood or plasma sample compressed between the raised seal head portions 78, chambers are formed by the opposed recessed portions 76. The chambers are provided in order to accommodate those portions of the tubing segment which are not to be compressed, but rather to be formed into pouches. Each chamber defined by each closed pair of recessed portions is configured to house a pouch.

A heater 82 is configured to heat each of the seal head portions of the platen in order for opposed raised portions to form a heat seal on the tubing segment when the sealing device is closed. The heater 82 may be any one of well known heater types such as radiant heaters, induction or resistance heaters, or the like. The heater 82 is preferably connected directly to each of the raised seal heads 78, to heat the raised portions without unduly heating the recesses. If desired, insulation can be provided to reduce heat transfer between the raised portions and the recesses. In an exemplary embodiment a cooling device 83 such as cooling or radiator fins, a moving air flow, or a cold finger may also be connected to the sealing device 70. The cooling device 83 is connected directly to each of the recessed portions 76 so that the chambers defined when opposed recessed portions move together are maintained at a low temperature. Blood or plasma samples contained in pouches formed within the chamber during the seal process are thus not damaged by the high temperatures of the heat seal.

Figure 3A:
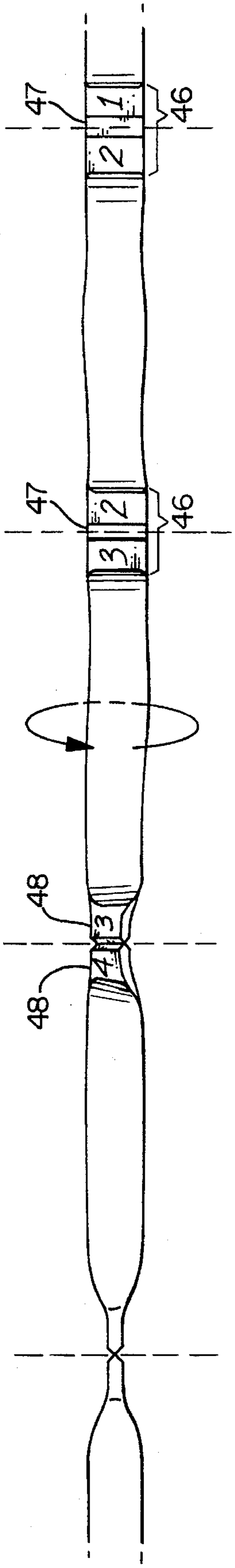
Figure 3B:
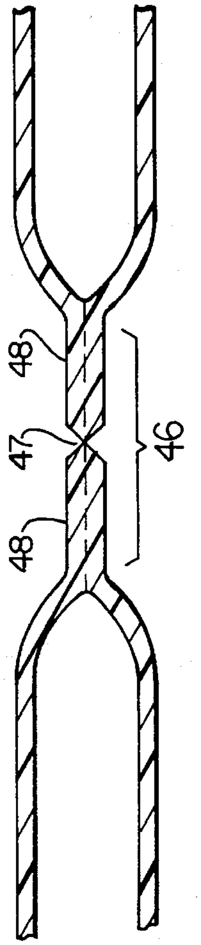

The narrow area (47 of FIG. 3*b*), through approximately the center of the seal, is formed by an elongated ridge structure 80 provided down the center of the extended portion 78 of the seal platens. As the tubing segment is squeezed between the upper and lower sealing heads, the ridge 80 forces an indentation on the top and bottom surface of the seal portion. The indentations narrow the plastic material comprising the center the seal, thus making it easy to separate.

In one embodiment of the invention, ridge 80 may be serrated in order to provide perforations disposed in a direction orthogonal to the major axis of the tubing segments. The perforations allow the individual and connected pouches to be removed from one another without the danger, inherent with cutting with a sharp object, of violating the integrity of a pouch by inadvertently cutting through to the sample containing area. The perforations are preferably provided during the seal process by providing the seal heads with serrations. Alternatively, perforations may be provided shortly thereafter, by use of a separate perforating jig or die.

Means 84 are also provided to open and close the sealing device 70 in order to compress the seal platens together and thus form seals along the length of the tubing segment. Such means are well known in the art and may suitably comprise a manual apparatus which opens and closes, such as a lever handle attached to one support frame and which moves the frame against, for example, a hinge. Other suitable arrangements may include vertical guides, spring or hydraulically operated piston presses or other common mechanical, electrical or hydraulic presses.

After sealing, the tubing segment is labelled on at least one end with a unique identifier that corresponds to the original plasma donation. This may be achieved by, for example, gluing a label onto the segment or by imprinting a bar coded emblem directly onto the tubing material. The tubing segment, including the sample containing pouches, is then frozen for preservation.

Returning to FIG. 2, it is important to be able to unambiguously identify all of the various parts of the system that comprise an individual plasma donation. Thus, unique identifiers such as coded threads, coded dots, bar codes, or other structure coded with the unique identifier may be placed in the physical structure of the plasma collection system. For example, in one embodiment a coded thread 37 is molded into the donation container 20, a coded thread 39 is molded along the edge of the bottle cap 22, a coded thread 41 is molded along the side of the test container 28, and a coded thread 43 is molded into the tubing segments at spaced-apart intervals. The unique identifier in the tubing segment runs along the length of the tubing segments and the code is repeated in order to permit segmentation of the tubing segments while maintaining identification integrity of each segment so prepared. Furthermore, each portion of the donation system is identified with the same code so that donation identity is maintained for all parts of the system.

Returning now to FIGS. 3*a*, 3*b*, and 4, it may be further desirable to have each individual pouch, along a segment, identified by an alpha or numeric code, equal to the position of the pouch along the linear length of the original tubing segment. Such code may be imprinted, for example, on the compressed portion of the seal pad located between adjacent pouches, by use of a stamping die. Such a stamping die may comprise an integral part of the sealing device as depicted in FIG. 4, so that sealing, forming pouches of variable sizes, and providing narrow or perforated areas for easy separation, as well as identification numbers, are all accomplished in a single efficient step. Alternatively, the alpha or numeric identifier could comprise part of a perforating jig or die.

Stamping dies are known which include means for advancing the alpha or numeric character to a next sequential one such that sequential pouches in a tubing segment are each identified by a corresponding sequential string of alpha (a, b, c, . . . ) or numeric (1, 2, 3, . . . ) characters.

Therefore, if a first testing pool is being prepared from pouches from several donations, a quality control check may be performed by confirming that all pouches to be pooled from each tubing segment have the same location code, for example, number 1. Likewise, when preparing a second testing pool from samples of the same donations, a quality control check may be performed by confirming that all pouches to be pooled from each tubing segment have, for example, the number 2 imprinted at some point on the compressed portion of the pouch.

In order to affect efficient PCR testing of a donation, the serology test sample, taken from each individual donation in test container 28 is tested for various known antigens and/or antibodies which are designated for specific viruses. If a sample is positive for one or more known antigen or antibody tests, the individual donation and its corresponding tubing segment are excluded from further testing and both may be disposed of in an appropriate manner.

Tubing segments, corresponding to the remaining serology negative donations, are divided into identified groups, each group comprising a selected number of donations. As will be described further below, the number of donations per group is determined by the sensitivity of the specific high sensitivity tests, such as a PCR test, the anticipated concentration of the viral RNA or DNA of interest in the plasma sample, and the anticipated frequency of a PCR positive sample occurring within the general donor population. For example, for the detection of the hepatitis-C virus, containing the RNA of interest, in a population of repeat plasmapheresis donors, it is appropriate to pool samples of between 100 and 700 individual donations. For a population in which viral contamination occurs more often, smaller pools of between 50 and 100 individual donations may be appropriate.

One embodiment of a process of preparing a PCR testing pool in accordance with the present invention will now be described in connection with FIGS. 5 and 6. A sampling plate 50, generally similar in application to a titer plate but configured in accordance with practice of the invention, is provided. The sampling plate 50 is configured to contain generally hemi-cylindrical sample wells 52, disposed horizontally on the plate in a generally regular array. A suitable sampling plate, used to practice the method of the invention, has 64 such sample wells arranged in a 8×8, row/column, rectangular fashion. A cover plate 54, having approximately the same exterior dimensions as the sampling plate 50 is also provided. The cover plate 54 is adapted to cover the surface of the sampling plate 50 in close-fit attachment. Through-holes 56 are arranged on the cover plate in the same array fashion as the sample wells of the sampling plate 50. When the cover 54 is placed over the surface of the sampling plate 50, through-holes 56 line up vertically over the sample wells 52, thereby allowing communication with the sample wells through the through-holes. The diameter of the through-holes is substantially smaller than the surface area of the test sample pouches, and the corresponding sample wells. However, the through hole diameter is sufficiently large to permit a needle, or other cannula like object, to pass through the holes and enter the sample wells beneath.

As shown in connection with FIG. 6, a terminal (first generation, "number 1") pouch 90 is removed from each tubing segment that has been identified as belonging to a particular PCR group to be tested. Each terminal pouch 90 is washed, but not opened, and placed in a corresponding sample well 52 of the sampling plate 50. The cover plate 54 is secured over the top of the sampling plate 50 and the plate, cover, and pouches are thawed at an appropriate temperature.

An equal volume of between about 0.02 to 0.5 ml of plasma is removed from each pouch and pooled in a testing container. A needle 92 or other cannula like device is inserted through the through-hole in the cover plate, and into the sampling plate sample well, directly below, thereby piercing the tubing material of the side wall of the pouch and gaining access to the plasma sample therein. In an exemplary embodiment, the needle is connected to a device that provides a continuous vacuum, or suction, to extract all of the blood or plasma contained in the pouch and minimize any leakage of fluid into the surrounding tray. The needle may be held in a device which allows the needle to move through the through-hole and top wall of the pouch, but restricts its downward progress so that the needle is prevented from touching or piercing the bottom wall of the pouch as the pouch sits in the sample well. When the cannula is withdrawn after extracting a sample, the cover plate material 94, surrounding the through-hole, prevents accidental withdrawal of the pouch along with the cannula, as depicted in FIG. 6.

While the method of preparing a PCR test pool has been described in terms of manually extracting a sample, by inserting a cannula individually into each sample well, the method may equally be practiced using an automated process. The sampling plate containing pouches in each well may be held so as to allow an array of cannulas, arranged in a manner corresponding to the arrangement of through-holes in the cover plate, to be pressed down onto the sampling plate, thereby allowing all of the sample pouches to be pierced, and samples extracted therefrom, at the same time. Alternatively, a single cannula or cannula holding device may be automated or programmed to successively pierce and withdraw fluid from each pouch. In order to prevent carryover contamination, a clean cannula is used to withdraw samples for each pool.

Referring now to FIG. 7, there is shown a flow chart of a PCR test methodology according to the invention, which allows for the identification of a unique PCR positive donation with the fewest number of individual tests.

The process begins at block 100 with the definition of an appropriate initial pool size which, in turn, depends on various factors such as the frequency of occurrence of the virus of interest in the general donor population, the likely final concentration of viral DNA or RNA after dilution in the pool, and the like.

Although the PCR test is highly sensitive, and is capable of detecting a single virus in a contaminated sample, a virus must necessarily be present in the sample for the PCR test to provide a positive result. If, for example, a sample from a contaminated donation having a relatively low virus concentration is pooled together with a large number of uncontaminated samples, the concentration of virus in the resulting pool may be so low that there is a statistical probability that no virus is present in a sample taken from the pool for PCR testing. Such pools may, indeed, falsely test negative for viral contamination.

For example, if a 0.02 ml sample was prepared from a plasma donation contaminated with viruses at a concentration of 500 viruses per ml of sample, the 0.02 ml sample would comprise, on average, 10 viruses. If this 0.02 ml contaminated sample were pooled with approximately 500 other 0.02 ml samples from uncontaminated donations, the resulting 10 ml pool would comprises viruses at a concentration of 1 per ml. Accordingly, if a 1 ml sample were taken from the pool for PCR testing, there is a significant statistical probability that the PCR sample will contain no viruses.

Such low concentrations of virus contamination pose little threat for products produced from plasma, because several methods are available for inactivating viruses present in such low concentration donations. Such viral inactivation methods include the use of solvent/detergent or heating at over 60° C. for an appropriate time or the like. These methods, generally, are described as being capable of reducing the concentration of viruses by a number of log units. For example, the solvent detergent method is capable of reducing the viral contamination of hepatitis-C by at least $10^7$ per ml or 7 logs units. Thus, plasma products such as factor VIII, factor IX or prothrombin complex may be prepared from plasma donations routinely treated by, for example, the solvent detergent method after having been PCR tested negative.

For blood products, routinely transfused directly to a recipient, there remains some small risk of low concentration viral contamination, after such donations have PCR tested negative.

In the embodiment illustrated in connection with FIG. 7, the factors discussed above, such as the frequency of occurrence of the virus of interest in the donor population, and the likely concentration of the virus after dilution, are evaluated. An appropriately sized first level PCR testing pool is designed which minimizes the statistical probability that viruses present in low concentrations will go undetected. The pool is prepared at block 101 by pooling the contents of terminal pouches of identified tubing sections, in the manner described above. At block 102, a PCR test is performed on the first level PCR pool.

Block 103 represents a decision point, in the methodology of the invention, which depends on the results of the PCR test performed in block 102. In the event of a negative result on the test, all of the donations, corresponding to samples used to make up the first level PCR pool, are presumed to be free of viral contamination, and released for further processing into pharmaceutical products. The methodology thus exits on receipt of a negative PCR test result.

When the PCR test returns a positive indication, this indicates that a viral contaminant is present in one, or more than one, of the donations which made up the original PCR first level pool. At block 104, an additional sample pouch, the pouch next to the one first removed, is taken from tubing segments which correspond to donations comprising the original PCR first level pool. These additional sample pouches are divided into two approximately equal subgroups, designated A and B herein for purposes of clarity.

These subgroups are then separately pooled, using a separate, clean cannula to form each subgroup pool in the same manner as described above, and only one of the subgroup pools is PCR tested, as indicated at block 105. It is immaterial, for purposes of the invention, which of the two subgroups is tested. In block 105, subgroup A is identified as the subgroup to be tested, but subgroup B could just as easily have been designated, without disturbing the methodology of the invention.

At block 106, a decision is made depending on the outcome of the PCR test of subgroup pool A. In the event that subgroup pool A tests negative for a PCR viral indication, no further testing is performed on samples from donations that comprised subgroup A. Rather, as indicated at block 107, the next sample pouches in sequence are taken from tubing segments that comprised subgroup B, which are then, in turn, divided into two approximately equal subgroups A' and B' Each subgroup, in this step, comprises approximately half the number of samples as comprised the immediately preceding subgroup. The contents of the subgroup sample pouches are again pooled separately, in the same manner as described above.

In the event that subgroup A tested PCR positive, indicating at least one of its component donations was virus contaminated, the other, untested subgroup (subgroup B in the example of FIG. 7) is now PCR tested, at block 108, to confirm that it is not, also PCR positive. Subgroup A now becomes the subgroup further subdivided into two approximately equal subgroups (A' and B') as indicated at block 109.

At block 110, PCR testing is performed on only one of the subgroup pools, A' or B', defined in preceding step 107 or 109. The method now iterates and returns to block 106 wherein the decision step is applied to the results of the PCR test performed at block 110. Again, if the PCR test results prove negative for the tested subgroup, the untested subgroup would be further subdivided into two approximately equal subgroups, each comprising approximately half the samples of the preceding subgroup. If the tested subgroup returned a PCR positive result, the tested subgroup would be further subdivided into two approximately equal subgroups, each of which would comprise one half of the samples of the preceding subgroup. In this case, the untested subgroup would again be PCR tested in order to confirm that it was not also PCR positive.

The test methodology continues iterating from block 106 through block 110 until testing is determined to be complete. Test completion is defined as when a subgroup division results in the creation of two subgroups, each containing only one sample pouch corresponding to a single donation. One of the samples is PCR tested at block 110 and if the test results are negative, the other sample is identified as belonging to a virally contaminated plasma donation. If the tested sample tests positive, the remaining sample is then also PCR tested in order to confirm that it is not also PCR positive.

Upon completion of all testing the methodology of the invention ends at block 111. It should be clear from the flow chart of FIG. 7, that the testing methodology of the invention only requires that two PCR tests be performed at each test level when the initially tested pool is positive: One initial test for one of the two subgroups, and one subsequent test to confirm that the corresponding initially untested pool is indeed negative. The test methodology requires only a single PCR test at each test level when the initially tested pool is negative.

Application of the system and method for sample testing of the invention will now be described in connection with a particular PCR test pool size, as depicted in FIG. 8. In FIG. 8, the terminal pouches of 512 individual donations are formed into an initial PCR testing pool at 201. For purposes of illustration, it will be assumed that only one of the 512 samples was taken from a donation which was contaminated by a virus of interest. The tubing segment depicted in FIG. 8 which comprises 10 individual and connected pouches, represents the tubing segments originally connected to, and taken from the contaminated plasma donation container.

The initial 512 sample pool is PCR tested, and because of the presence of the contaminated sample, returns a positive viral indication. At step 202, two 256 donation pools (256A and 256B) are prepared from the next sequential pouches taken from segments that made up the prior positive pool. Pool 256B is now PCR tested and, as depicted in FIG. 8, returns a negative viral indication, thus indicating that pool 256A contains a sample from the contaminated donation.

At step 203, two 128 donation pools are prepared from the next sequential pouches of tubing segments that made up pool 256A. Thus, according to the invention, pool 256A has been subdivided without having been PCR tested. At step 203, pool 128A is now PCR tested and, since it returns a negative viral indication, pool 128B is now known to include a sample pouch from the contaminated donation. Pool 128B is then subdivided into two 64 donation pools (64A and 64B) by removing the next sequential pouch from those tubing segments whose preceding pouches made up pool 128B.

Next, pool 64B is PCR tested and, in the example of FIG. 8, returns a positive viral indication. In this case, PCR testing is performed on pool 64A in order to verify that it is, indeed, negative and that no additional contaminated samples are present beyond those in pool 64B. At step 205, pool 64B is further subdivided into two 32 donation pools, 32A and 32B, by removing the next sequential pouch from tubing segments used to make up preceding pool 64B. Pool 32B is PCR tested, returns a negative viral indication, as indicated, and pool 32A is therefore further subdivided into two 16 donation pools, 16A and 16B. Again, the 16 donation pools are prepared by removing the next sequential sample pouch from tubing segments that made up the preceding positive pool, 32A.

At step 206, pool 16B is PCR tested and returns a positive viral indication. Pool 16A, therefore, is PCR tested in order to confirm that it is negative, and that all contaminated samples are present in pool 16B.

At 207, pool 16B is subdivided into two 8 donation pools, 8A and 8B, by removing the next sequential sample pouch from tubing segments that made up the preceding positive pool 16B. Pool 8B is then PCR tested and, as illustrated, returns a negative viral indication, indicating that pool 8A contains a sample from a contaminated donation. Pool 8A is then further subdivided into two 4 donation pools, 4A and 4B, at step 208. PCR testing is performed on pool 4B, which returns a negative indication, thus indicating that pool 4A contains a sample from a contaminated donation. Pool 4A is then subdivided, at 209, into pools 2A and 2B in the same manner, as described above. Upon PCR testing, pool 2A returns a negative viral indication indicating that one of the two samples comprising group 2B was taken from a tubing segment of a corresponding contaminated donation.

At step 210, the individual donations are tested by removing the final pouch from the tubing segments that made up group 2B. The final individual donations are PCR tested in order to identify the specific positive donation, which is then removed from storage and appropriately disposed of. The remaining 511 viral free donations are retained for further processing into pharmaceutical products.

In the above example, a single contaminated donation has been uniquely identified from a group of 512 such donations, by performing only 13 separate PCR tests, including the primary PCR test on the original 512 donation pool. The method of the invention, allows for skipping a PCR test on a particular subpool, so long as the corresponding tested subpool returns a negative viral indication. By thus skipping certain PCR tests, the method of the invention reduces the number of PCR tests that must be performed in order to identify a specific positive donation, without sacrificing the resolution of the PCR test methodology. Under the method of the invention, all positive donations will be identified but without requiring that all donations be tested.

From the exemplary embodiment of FIG. 8, it will be clear that either one of the successively smaller subgroups may be PCR tested and that the arbitrary position of the positive sample may be varied. Thus, if a sample from the positive donation were present in each initially tested subpool, 18 tests would be required to uniquely identify the positive donation (one initial test which returns a positive indication and one additional test to assure that the corresponding subpool is negative).

By the same token, if each initially tested subpool returns a negative indication, 10 tests would be required to identify the positive donation. In practice, positive and negative test results on the subpools would tend to distribute equally, thus, 14 tests on average would be required to identify a uniquely positive donation from an initial donation pool for 512 units.

It is, therefore, clear from the foregoing that the system and method of the present invention, including the provision of tubing segments comprising individual and connected pouches each containing a sample of a plasma donation, is advantageous in providing a multiplicity of PCR test pools. Unlike conventional pool preparation, in which a sequence of initial and subsequent pools are formed from a single sample of each donation at the same time, the present invention allows for formation of a test pool immediately prior to testing. This manner of "just-in-time" pool formation permits construction of test pools from individual pouches only as needed. The possibility of contamination is eliminated since the pools are constructed at different times, each from sealed sample pouches. Moreover, sample pouches remain frozen until needed to develop a test pool. Multiple freeze-thaw cycles which may adversely affect the recovery of the DNA or RNA of interest are avoided, thus insuring the integrity of the PCR test.

Accordingly, the practice of the present invention results in the blood supply, and blood or plasma products prepared therefrom, being substantially safer by virtue of its being as free as possible from viral contamination. Advantageously, cost effective, high sensitivity testing is readily performed for the presence of a virus directly. Thus, false indications of virus contamination usually associated with antibody testing during the infectivity window period, is avoided. Moreover, the present invention allows cost effective use of high sensitivity tests which are capable of detecting the presence of a single virus in the test sample, thus helping insure the freedom of the blood supply from incipient viral contamination.

Those skilled in the art will appreciate that the foregoing examples and descriptions of various preferred embodiments of the present invention are merely illustrative of the invention as a whole, and that variations in the shape, size and number of the various components of the present invention, as well as the types of tests implemented, may be made within the spirit and scope of the invention. For example, it will be clear to one skilled in the art, that the length of the individual and connected pouches, and therefore their volumetric content, may be progressively increased along the length of the tubing segment. As successive testing subpools are formed from a smaller and smaller number of samples, the volume of plasma comprising the pool necessarily decreases. It should be clear, that in order to maintain a sufficient volume of plasma in each successive subpool, successive sample pouches may contain a larger volume in order to accommodate a desired final pool volume. In order to accommodate pools ranging in size from about 1 ml to about 10 ml, it will be clear that the volumes of successive sample pouches will increase from about 0.02 ml to about 0.5 ml, in progressive steps. In one exemplary embodiment the pouch volume is 0.02 ml in the first pouch to be used in the largest pool and is 0.2 ml in the final pouch.

It will also be clear to those skilled in the art that the system of the invention is not limited to the exemplary plasma collection container and an associated tubing segment. Blood bags, or other biological fluid containers may be used with equal facility, and that suitable tubing segments may be attached thereto both prior to fluid collection and after fluid collection is completed. All that is required is that sample quantities of biological fluids be transferred to a tubing segment which is then formed into pouches in accordance with practice of the invention.

Accordingly, the present invention is not limited to the specific embodiments described herein, but rather is defined by the scope of the appended claims.

What is claimed is:

1. A process for preparing samples of blood or plasma for planned high sensitivity testing, the samples being drawn from a collection container containing a blood or plasma donation and having a flexible hollow tubing segment connected thereto and open to the inside of the container, the process comprising the steps of:

withdrawing a blood or plasma sample from the collection container by transferring said blood or plasma from the container to the flexible tubing segment, thereby filling the tubing segment;

sealing a portion of the tubing segment at both ends;

removing the sealed portion of the tubing segment from the container;

providing a plurality of spaced-apart seals at intervals along the length of the removed tubing segment, the segment portions in the intervals between the seals defining pouches, wherein the spaced-apart seals are formed by providing elongated first and second opposing seal platens comprising a plurality of recessed portions and raised portions spaced-apart from each other along the length of the platens, closing together said opposed seal platens onto the removed tubing segments so that the raised portions compress and heat the portions of the tubing located between said raised portions to thereby form said plurality of spaced-apart seals, the opposed recessed portions forming chambers configured to house the pouches defined between said seals, wherein each such pouch contains a blood or plasma sample, and wherein the intervals between pouches are selected to provide at least a sufficient volume in the pouches for the planned testing; and labelling the removed tubing segment with a unique identifier corresponding to the donation.

2. A process according to claim 1 wherein the tubing segment is constructed of plastic and the tubing segment label further comprises a coded thread molded into the plastic and disposed along the major axis of the tubing segment.

3. The process according to claim 2 wherein the coded thread comprises a code which repeats at spaced apart intervals, the code intervals corresponding to at least the intervals of the segment portions defining the pouches, wherein each pouch contains at least one cycle of said code.

4. A process according to claim 1 wherein each of said plurality of spaced apart seals includes perforations in a direction orthogonal to the major axis of the tubing segment.

5. The process according to claim 1 wherein each of said plurality of spaced apart seals includes at least a pad portion having dimensions sufficiently large to permit separating the pouches by cutting through said pad portion without compromising the integrity of the pouch.

6. The process according to claim 1 wherein each of said plurality of spaced apart seals includes indicia for identifying a sequential position of a corresponding pouch along the length of said tubing segment.

7. The process of claim 1 wherein the sample is a plasma sample.

8. The process of claim 1 wherein the sample is a blood sample.

9. A process for preparing blood or plasma samples for planned testing, the process comprising the steps of:

providing a blood or plasma donation in a collection container;

attaching a flexible hollow tubing segment to the container the tubing segment open to the inside of the container;

filling the tubing segment with the blood or plasma from the collection container;

sealing a portion of the tubing segment at both ends;

removing the sealed portion of the tubing segment from the container; and either before or after the sealed tubing segment portion is removed from the container; and providing a plurality of spaced-apart seals at intervals along the length of the tubing segment between the sealed ends, the segment portions in the intervals between adjacent seals defining pouches, wherein the spaced-apart seals are formed by providing elongated first and second opposing seal platens comprising a plurality of recessed portions and raised portions spaced-apart from each other along the length of the platens, closing together said opposed seal platens onto the removed tubing segments so that the raised portions compress and heat the portions of the tubing located between said raised portions to thereby form said plurality of spaced-apart seals, the opposed recessed portions forming chambers configured to house the pouches defined between said seals, wherein each such pouch contains a plasma or blood sample and wherein the intervals between seals provide a sufficient volume in each such pouch for the planned testing.

10. The process according to claim 9, wherein the tubing segment is constructed of plastic and is labelled with a unique identifier corresponding to the donation.

11. The process according to claim 10, wherein the tubing segment label comprises a coded thread molded into the plastic and disposed along the major axis of the tubing segment.

12. The process according to claim 11, wherein the coded thread comprises a code which repeats at spaced-apart intervals, the code intervals corresponding to at least the intervals of the segment portions defining the pouches, and wherein each such pouch contains at least one cycle of said code.

13. The process according to claim 9, wherein each of said plurality of spaced-apart seals includes indicia for identifying a sequential position of a corresponding pouch along the length of said tubing segment.

14. The process according to claim 9, wherein the sample is a plasma sample.

15. The process according to claim 9, wherein the sample is a blood sample.

16. A process for preparing a plasma pool from a multiplicity of separate plasma donations, the process comprising:

providing a plurality of separate plasma donations;

drawing a plasma sample from each donation into a corresponding flexible hollow tubing segment;

providing a plurality of spaced-apart seals at intervals along the length of each tubing segment, the segment portions in the intervals between the seals defining pouches, each pouch containing a plasma sample;

removing a first pouch from each of said tubing segments;

withdrawing a portion of the contents of each said first pouches; and pooling the withdrawn portions of each pouch in a container.

17. The process according to claim 16, wherein the hollow tubing segment comprises plastic which incorporates an elongated coded indicia molded into the plastic and disposed along the major axis of the tubing segment.

18. The process according to claim 17, wherein the coded indicia comprise a thread which includes a code which repeats itself at spaced-apart intervals, the code intervals corresponding to at least the intervals of the segment portions defining the pouches, wherein each such pouch contains at least one cycle of said code.

19. The process according to claim 16, wherein each of said plurality of spaced-apart seals includes perforations in a direction orthogonal to the major axis of the tubing segment.

20. A process for preparing a plasma pool from a multiplicity of separate plasma donations, the process comprising:

providing a plurality of separate plasma donations;

drawing a plasma sample from each donation into a corresponding flexible hollow tubing segment;

providing a plurality of spaced apart seals at intervals along the length of each tubing segment, the segment portions in the intervals between the seals defining pouches, each pouch containing a plasma sample;

providing a sampling plate, the sampling plate having a plurality of receptacles disposed in a regular array;

providing a cover adapted to fit over the sampling plate, the cover having a plurality of holes formed therethrough, the holes disposed in a regular array and arranged such that each hole is positioned over a corresponding receptacle in the sampling plate, each hole having a size sufficient to permit entry of a cannula into said corresponding receptacle through said hole;

removing a first pouch from each of said tubing segments;

placing each of said first pouches into a separate receptacle of the sampling plate;

placing the cover over the pouches to thereby secure the pouches in the receptacles;

inserting a cannula into each receptacle, through a corresponding hole in said cover, thereby piercing each said pouch and putting the cannula into communication with the plasma sample contained therein;

withdrawing a portion of the contents of each said pouch; and pooling the content portions of each pouch in a container.

21. The process according to claim 20 wherein said sampling plate receptacles comprise hemi-cylindrical sample wells elongated in a horizontal direction.

22. A process according to claim 20 wherein said portion of the contents withdrawn from each said pouch is from about 100 to about 200 microliters.

23. A process according to claim 20 wherein said sampling plate comprises 64 receptacles disposed in a regular 8×8 array.

24. A process according to claim 20 wherein said sampling plate comprises 100 receptacles disposed in a regular 10×10 array.

25. The process according to claim 20 wherein said cannula is inserted into each receptacle and a portion of the contents of each said pouch is withdrawn in sequential fashion.

26. A process for testing a multiplicity of plasma donations to uniquely identify donations having a positive viral indication, the process comprising the steps of:

(a) providing a plurality of plasma donations, wherein a portion of each donation is contained in a tubing segment divided along its length by spaced apart seals, the tubing segment portions between the seals defining sequential pouches, wherein each pouch contains a plasma sample of said donation;

(b) removing a first pouch from each said tubing segment corresponding to each donation;

(c) forming the contents of each first pouch into a first pool;

(d) testing said first pool for a viral indication;

(e) when said first pool tests positive for said viral indication removing a next sequential pouch from each of the tubing segments used to form said first pool;

(f) dividing the next sequential pouches into two approximately equal next generation subgroups and separately forming the contents of the subgroup pouches into pools;

(g) testing one of said subgroup pools for the presence of a specific virus;

(h) when the tested subgroup pool tests negative for said virus removing a further sequential pouch from corresponding tubing segments used to form the untested subgroup;

(i) dividing said further sequential pouches into two approximately equal and successively smaller subgroups and separately forming the contents of the subgroup pouches into pools; and (j) testing one of said subgroup pools for a viral indication.

27. A process according to claim 26 further comprising the steps of:

(k) when said tested subgroup pool tests positive in step (g) for said viral indication, removing a further sequential pouch from corresponding tubing segments used to form said tested subgroup;

(l) dividing said pouches into two approximately equal and successively smaller subgroups and separately forming the contents of the subgroup pouches into pools; and (m) testing one of said subgroup pools from step (e) for a viral indication.

28. A process according to claim 27 further comprising:

when said tested subgroup tests positive in step (g) for said viral indication, the additional step of testing the untested one of the subgroups for a viral indication.

29. A process according to claim 28 further comprising:

repeating the process of steps (h) through (m), wherein successively smaller subgroups are formed from corresponding tubing segments used to form an immediately preceding positive subgroup until each said smaller subgroup comprises the contents of a single pouch corresponding to a single donation;

testing the contents of one of said single pouches for a viral indication; and determining whether the donation corresponding to the contents of said tested pouch is PCR positive in response to said test.

30. A process for testing a multiplicity of plasma donations to uniquely identify donations having a positive viral indication, the process comprising the steps of:

providing a plurality of plasma donations, wherein a portion of each donation is contained in a tubing segment divided along its length by spaced apart seals, the tubing segment portions between the seals defining sequential pouches, wherein each pouch contains a plasma sample of said donation;

removing a first pouch from each said tubing segment and forming the contents of each first pouch into a first pool;

testing said first pool for a viral indication;

when said first pool tests positive for said viral indication removing a next sequential pouch from each of the tubing segments used to form said first pool;

dividing said next pouches into two approximately equal subgroups and separately forming the contents of the subgroup pouches into pools;

testing one of said subgroup pools for a viral indication;

when said tested subgroup pool tests positive for said viral indication removing a further sequential pouch from corresponding tubing segments used to form said tested subgroup;

dividing said further pouches into two approximately equal next generation subgroups and separately forming the contents of the subgroup pouches into pools;

testing the untested one of the subgroups for a viral indication; and testing one of said next generation subgroup pools for a viral indication.

31. A process according to claim 30 further comprising the steps of:

when the tested one of said subgroup pools tests negative for said viral indication removing a further sequential pouch from corresponding tubing segments used to form the untested subgroup;

dividing said further pouches into two approximately equal next generation subgroups and separately forming the contents of the subgroup pouches into pools; and testing one of said next generation subgroup pools for a viral indication.

* * * * *